United States Patent [19]

Taniguchi et al.

[11] Patent Number: 4,975,568
[45] Date of Patent: Dec. 4, 1990

[54] CONTAINER INSPECTING APPARATUS WITH A LIGHT SHIELDING MEMBER SHAPED TO CONTAINER PROFILE

[75] Inventors: Shin ichi Taniguchi, Osaka; Takashi Ohtsuki, Kawabe, both of Japan

[73] Assignee: Takeda Chemical Industries, Ltd., Osaka, Japan

[21] Appl. No.: 307,288

[22] Filed: Feb. 7, 1989

[30] Foreign Application Priority Data

Feb. 10, 1988 [JP] Japan ................................. 63-29551

[51] Int. Cl.$^5$ ......................... G01N 9/04; G01N 21/16
[52] U.S. Cl. ............................. 250/223 B; 250/237 R; 356/240
[58] Field of Search ............... 250/223 B, 223 R, 224, 250/234, 235, 237 R; 356/240; 209/526, 524, 522, 529; 358/106

[56] References Cited

U.S. PATENT DOCUMENTS

| 3,029,349 | 4/1962 | Schell | 250/223 B |
|---|---|---|---|
| 3,411,009 | 11/1968 | Ford et al. | 250/223 B |
| 3,963,348 | 6/1976 | Nakatani et al. | 250/223 B |
| 4,079,416 | 3/1978 | Faani et al. | 358/106 |
| 4,108,762 | 8/1978 | Babunovic et al. | 356/240 |
| 4,676,650 | 6/1987 | Bjorndal et al. | 356/427 |

FOREIGN PATENT DOCUMENTS

| 0156346 | 10/1985 | European Pat. Off. |
|---|---|---|
| 0203605 | 12/1986 | European Pat. Off. |
| 41-9079 | 5/1941 | Japan ........................ 250/223 B |

*Primary Examiner*—David C. Nelms
*Assistant Examiner*—Michael Messinger
*Attorney, Agent, or Firm*—Wenderoth, Lind & Ponack

[57] ABSTRACT

An inspecting apparatus includes an illuminator, a light sensor positioned on one side of the path of movement of containers opposite to the illuminator capable of receiving rays of light which have passed through the container, rays of light reflected fro the container and rays of light travelling straight from the illuminator towards the light sensor within a predetermined region exteriorly of the container, a detector for analyzing the rays of light received by the light sensor, and a light absorbing or shielding member positioned diagonally and to the side of the container as viewed in a direction from the light sensor towards the illuminator. The light absorbing or shielding member shields rays of light reflecting from the surfaces of each of opposite wall portions of the container. Thus, a line of shade corresponding to the contour of the container can be formed on the side of the light sensor for accentuating the boundary between the container, illuminated by the rays of light from the illuminator, and a predetermined region defined exteriorly of the ocntainer by the rays of light travelling striaght towards the light sensor.

9 Claims, 5 Drawing Sheets

CONTAINER INSPECTING APPARATUS WITH A LIGHT SHIELDING MEMBER SHAPED TO CONTAINER PROFILE

BACKGROUND OF THE INVENTION

1. Field of Technology

The present invention generally relates to an apparatus for inspecting transparent containers such as, for example, transparent ampoules.

2. Description of the Prior Art

Hitherto, the presence or absence of foreign matter afloat or settling in a liquid medium filled in each ampoule or the like, or that of cracking in the wall forming each ampoule or the like, is automatically detected by analyzing rays of light propagating towards and reflected from the ampoule or the like. However, when it comes to the detection of the presence or absence of flaws in the outwardly tapering throat of each ampoule, automatic detection has not yet been employed and an inspector is used to perform a visual inspection.

The flaws which would generally be found in each ampoule and of which detection has not yet been automated include a bending of the ampoule throat laterally from the longitudinal axis of the ampoule, a filament-like bleeder left unremoved at the closed tip of the ampoule throat, a variation in wall thickness of the ampoule throat, undesirable adherence of foreign matter to one or both of the inner and outer surfaces of the ampoule throat, and so on.

Currently, a method has generally been practiced to detect an abnormal change in a waveform of a video signal supplied from a video camera. However, when it comes to a transparent or substantially transparent container, it is difficult to discriminate between the background light and the light which has been transmitted through the transparent container or which has been reflected from the wall forming the container and, moreover, where the throat is slightly bent relative to the body, the determination of whether the container being inspected is acceptable or whether it is defective and is, hence, to be rejected, in reliance on the image processing technique is not easy because the coverage of inspection varies with the rotation of the container being inspected unless use is made of a complicated and expensive machine system.

SUMMARY OF THE INVENTION

Accordingly, an object of the present invention is to provide an inspecting apparatus for the inspection of a substantially transparent container, which apparatus is capable of accentuating the appearance of the substantially transparent container so that the processing of a signal waveform representative of an image of the transparent container can be simplified by discriminating between the background light and the light having passed through the transparent container.

In order to accomplish the above-described object of the present invention, the inspecting apparatus according to the present invention comprises a source of illuminating light positioned on one of opposite sides of a substantially transparent container; a light receiving means positioned on the other of the opposite sides of the substantially transparent container for receiving rays of light which have passed through the substantially transparent container, rays of light reflected from the substantially transparent container and rays of light travelling straight from the illuminating light source towards the light receiving means within a predetermined region defined exteriorly of the substantially transparent container; a detecting means for analyzing the rays of light received by the light receiving means; and a light absorbing unit positioned rearwardly and to the sides of the substantially transparent container as viewed in a direction from the light receiving means towards the illuminating light source for shielding rays of light reflected at inner and outer surfaces of each of opposite wall portions of the substantially transparent container, whereby a line of shade corresponding to the contour of the substantially transparent container can be formed on the side of the light receiving means for accentuating the boundary between the substantially transparent container, illuminated by the rays of light from the illuminating light source, and the predetermined region defined exteriorly of the substantially transparent container by the rays of light travelling straight towards the light receiving means.

More specifically, the apparatus according to one aspect of the present invention comprises:

a source of illuminating light positioned on one of opposite sides of a substantially transparent container and spaced a predetermined distance therefrom for illuminating a portion of the substantially transparent container, which is to be inspected, defined between circumferentially spaced opposite wall portions of the substantially transparent container, as well as the surroundings of the substantially transparent container;

a light receiving means positioned on the other of the opposite sides of the substantially transparent container for receiving rays of light from the illuminating light source;

a light absorbing member disposed between the illuminating light source and the substantially transparent container and operable to permit the passage therethrough towards the light receiving means of rays of light which have passed through that portion of the substantially transparent container to be inspected, and of rays of light travelling straight from the illuminating light source towards the light receiving means within a predetermined region defined exteriorly of the substantially transparent container without passing through the substantially transparent container, and also operable to shield rays of light which include mainly rays of light propagating from the illuminating light source by which would be refracted by and reflected from inner and outer surfaces of the substantially transparent container before they impinge upon the light receiving means, wherefore the first- and second-mentioned rays of light are allowed to be received by the light receiving means while the third-mentioned rays of light are shielded from being received by the light receiving means; and a detecting means for examining the rays of light having passed through that portion of the substantially transparent container which is bound inside the circumferentially spaced opposite wall portions of the substantially transparent container, to detect an abnormality which would be present in the substantially transparent container.

According to another aspect of the present invention, there is provided an inspecting apparatus for the inspection of the substantially transparent containers, which apparatus comprises a light receiving and processing device capable of receiving rays of light, which have been passed through the substantially transparent container held at an inspecting position, rays of light reflected from the substantially transparent container and rays of light which have not passed through the substantially transparent container (that is, rays of light passing exteriorly of the substantially transparent container), said inspecting position being defined on a path of travel of the substantially transparent containers which are successively transported in one direction, said substantially transparent container at said inspecting position being rotated about a longitudinal axis thereof perpendicular to said one direction; and a light absorbing unit disposed generally rearwardly and to the sides of the substantially transparent container as viewed in a direction from the light receiving and processing device.

Preferably, a means for transporting the substantially transparent containers in the inspecting apparatus is a wheel, and the light absorbing member is a generally comb-shaped light absorbing ring mounted coaxially with the wheel. As an illuminating light source, a flat panel type illuminator may be employed and disposed inside a predetermined position on the path of travel of the substantially transparent containers and on the wheel. A light receiving and detecting means (the light receiving and processing device) may be employed in the form of a video camera which may be positioned outside said predetermined position.

For the purpose of the present invention, the term "container" herein referred to is to be understood as meaning of a type having a longitudinal axis and also having an appearance substantially symmetrical about the longitudinal axis.

Also, the term "transparent (container)" hereinabove and hereinafter referred to is to be understood as including not only a container either totally transparent or partly transparent, but also a container either totally semitransparent or partly semitransparent, regardless of whether it is colored or colorless. Specifically, the present invention is operable with any container provided that at least a portion of the container to be inspected is substantially transparent (i.e., either transparent or semitransparent) regardless of whether it is colored or colorless.

Again, the term "light absorbing member" hereinbefore and hereinafter referred to and used for the purpose of describing the present invention is intended to mean material having a capability of absorbing light (in a quantity about 50% or more) when rays of light from the illuminating light source impinge thereupon. Although in general any material, for example, a light source or a mirror in extreme cases, may absorb light, no strict interpretation is necessary in the practice of the present invention and, where rays of light sensed by the light receiving means are of, for example, a visible wavelength, the light absorbing member may have a black surface or a colored or colorless surface having a low brightness (for example, 6 to 9).

BRIEF DESCRIPTION OF THE DRAWINGS

This and other objects and features of the present invention will become clear from the following description taken in conjunction with a preferred embodiment thereof with reference to the accompanying drawings, in which:

FIG. 1 illustrates the principle of an ampoule inspection system according to the present invention, wherein

DETAILED DESCRIPTION OF THE PREFERRED EMBODIMENT

Before the detailed description proceeds, it is to be noted that, since the present invention is suited for use with transparent ampoules of a type generally used in the pharmaceutical field and having a substantially cylindrical body closed at one end by a bottom wall and a generally outwardly tapering coaxial throat connected thereto by a neck region intermediate the body and the throat, reference will be made to such ampoules as items to be inspected by the apparatus of the present invention.

The principle of the present invention will first be discussed with particular reference to FIGS. 1 to 5.

Referring first to FIG. 1, the throat of the ampoule, hereinafter referred to as an ampoule throat, is identified by 1 and shown in sectional representation taken in a direction perpendicular to the longitudinal axis thereof. A flat panel type illuminator 2 capable of providing collimated rays of light is disposed rearwardly of the ampoule throat 1 and on one of opposite sides of the ampoule throat 1, while a light sensor 3 is disposed forwardly of the ampoule throat 1 and on the other of the opposite sides of the ampoule throat 1 and oriented perpendicular to the illuminator 2.

A light absorbing member 4 is disposed generally rearwardly and to the side of the ampoule throat 1, that is, between the illuminator 2 and the ampoule throat 1, and has a light shielding layer 8 formed on one surface thereof confronting the ampoule throat 1 and the light sensor 3.

Rays of light emanating from the illuminator 2 and eventually received by the light sensor 3 generally include tangential and straight rays of light P1, refracted rays of light P2 and transmitted rays of light P3. The tangential and straight rays of light P1 are those which have not passed through the ampoule throat 1 and have passed exteriorly of the ampoule throat 1; the refracted rays of light P2 are those which, after having entered each of circumferentially opposite lateral portions of the circumferential wall 1a of the ampoule throat 1 which are spaced in a direction generally parallel to the illuminator 2, have passed only through such opposite portions of the wall 1a and subsequently emerge therefrom and propagate towards the light sensor 3; and the transmitted rays of light P3 are those which are transmitted into the interior 1b of the ampoule throat 1 through one (a rear wall portion) of circumferentially opposite wall portions of the wall 1a of the ampoule throat 1, which are spaced in a direction generally conforming to the optical axis perpendicular to the illuminator 2, and subsequently emerge from the ampoule throat 1 and propagate towards the light sensor 3 by passing through the other (a front wall portion) of the opposite portions of the ampoule throat 1.

In addition to the rays of light P1, P2 and P3, the rays of light falling on the light sensor 3 also include reflected rays of light P4 which do not emanate from the illuminator 2, but which originate from the outside of the ampoule throat 1 and are reflected from inner and outer surfaces of the circumferential wall 1a of the ampoule throat 1.

Most of the refracted rays of light P2 originating from the illuminator 2 and propagating toward the circumferential wall 1a of the ampoule throat 1 are reflected at the outer surface of the ampoule throat so as to travel outwardly from the ampoule throat 1 as indicated by P5, instead of entering the ampoule throat 1, and are reflected at the inner surface of the ampoule throat 1 so as to travel outwardly from the ampoule throat 1 as indicated by P6, instead of emerging outwardly from the circumferential wall 1a of the ampoule throat 1. Since those rays of light P5 and P6 do not fall on the light sensor 3, the amount of the refracted rays of light P2 actually received by the light sensor 3 is relatively small and, therefore, it is dark when only the opposite lateral portions of the circumferential wall 1a of the ampoule throat 1 are examined relying only on the refracted rays of light P2.

On the other hand, of reflected the rays of light P4 received by the light sensor 3, rays of light P4A reflected at the outer surface of the wall of the ampoule throat 1 and rays of light P4B reflected at the inner surface of the wall of the ampoule throat 1 after having passed through the wall 1a toward the interior 1b of the ampoule throat are so predominant in quantity that, when the reflected rays of light P4A and P4B are superimposed with the refracted rays of light P2, the opposite lateral portions of the wall 1a of the ampoule throat 1 will be highlighted.

Figures 1A, 2, 3:
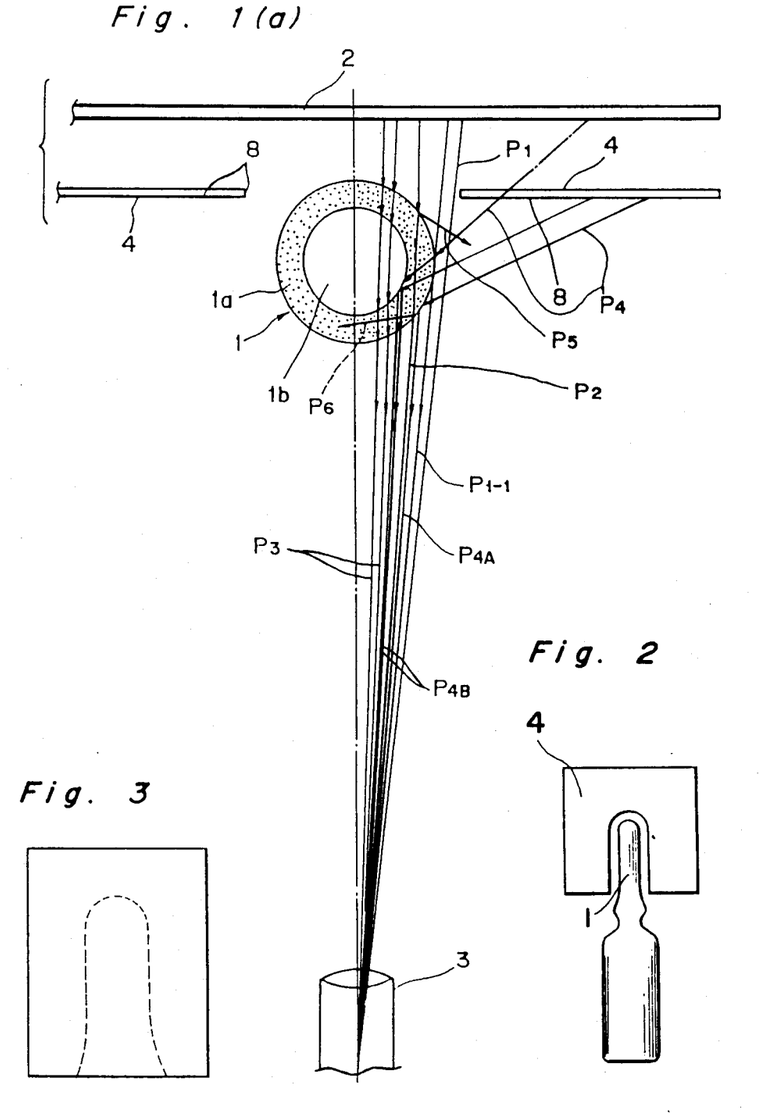
FIG. 1(a) is a diagram showing an overall structure of the ampoule inspection system and FIG. 1(b) is a diagram on an enlarged scale of a portion of the system shown in FIG. 1(a)
FIG. 2 is a schematic elevational view of an ampoule and a light absorbing member as viewed from the position of a light sensor shown in FIG. 1.
FIG. 3 is a schematic diagram showing an image of an ampoule throat as observed with no light absorbing member employed.

Accordingly, without the light absorbing member 4, an image observed of the ampoule throat 1 will be such as schematically shown in FIG. 3 wherein, since the outer contour of the ampoule throat 1 observable with the tangential and straight rays of light P1, the wall of the ampoule throat 1 observable mainly with the reflected rays of light P4A and P4B and the interior 1b of the ampoule throat 1 observable with the transmitted rays of light P3 are all highlighted, the boundary between the outer contour, wall and interior of the ampoule throat 1 cannot be distinctly observed, making it difficult to determine the entire cross-section of the ampoule to be examined defined within the opposite lateral portions of the wall of the ampoule throat 1.

According to the present invention, however, the light absorbing member 4 is positioned generally rearwardly and to the side of the ampoule throat 1 as hereinbefore described. With the light absorbing member 4 employed, the reflected rays of light P4 (including the rays of light P4A and P4B) are shielded from the light sensor 3 while the straight rays of light P1 passing laterally outwardly of the ampoule throat 1 towards the light sensor 3 are restricted to a predetermined range. In other words, referring particularly to FIG. 1(b), the position L of an inner edge 4a of the light absorbing member 4 is so selected as to lie outwardly of one of the tangential rays of light which, as indicated by P1-1, travel tangentially to the circumference of the wall 1a of the ampoule throat 1 from the illuminator 2 towards the light sensor 3 and to lie inwardly of the innermost one P4-1 of the reflected rays of light P4 with respect to the opposite lateral portions 1a' of the wall of the ampoule throat 1. Thus, by selecting the position L of the inner edge 4a of the light shielding member 4 so as to lie outside the tangential ray P1-1 and inside the reflected beam P4-1, the predetermined range for the straight rays of light P1 to be received by the light sensor 3 can be defined as indicated by W. Accordingly, by allowing the tangential and straight rays of light to travel straight towards the light sensor 3 within the predetermined range from the outer surface of each of the opposite portions of the wall 1a of the ampoule throat 1, a bright region of a predetermined width can be obtained on each side of the ampoule throat 1 and, at the same time, since the ampoule throat 1 is positioned inwardly of the innermost reflected beam P4-1 travelling tangentially to the circumference of the wall of the ampoule throat 1, all of the reflected rays of light P4 travelling on one side of the innermost reflected beam P4-1 relative to the ampoule throat 1 can be advantageously shielded from falling on the light sensor 3.

Figures 1B, 4:
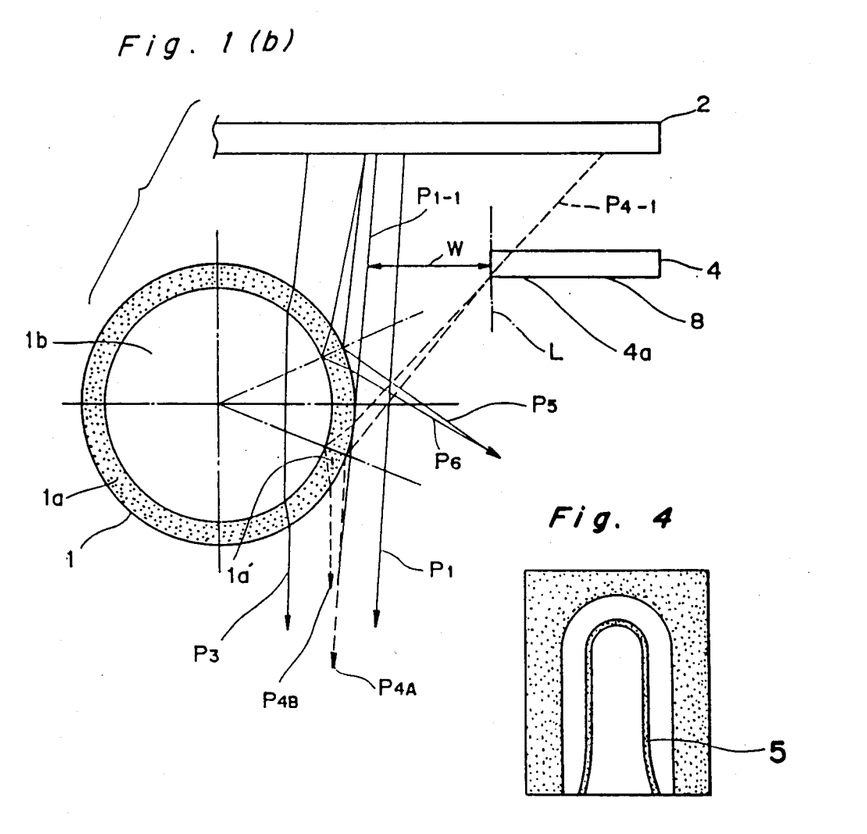
FIG. 4 is a schematic diagram showing an image of the ampoule throat as observed with the light absorbing member employed.

As hereinbefore discussed, the use of the light absorbing member 4 is effective to shield the reflected rays of light P4 passing through each of the opposite lateral portions of the wall 1a of the ampoule throat 1 from entering between the straight rays of light P1 and the transmitted rays of light P3 and from being superposed with the refracted rays of light P2, which are few and dark. Therefore, respective images observed of the opposite lateral portions of the wall 1a of the ampoule throat 1 are shaded to accentuate the contour of the ampoule throat 1. Also, as hereinbefore discussed, the light absorbing member 4 permits only the straight rays of light P1 within the predetermined range laterally outwardly of the outer surface of the ampoule throat 1 to pass therethrough towards the light sensor 3 while intercepting rays of light lying outside such a predetermined range. Therefore, a predetermined area proximate and surrounding the ampoule throat 1 can also be highlighted while areas other than such predetermined area are darkened. The image of the ampoule throat 1 so obtained will be such as shown in FIG. 4 wherein a line of shade 5 corresponds to the contour of the ampoule throat 1 while the outside and inside of the shade line 5 are bright. This means that the shade line 5 distinguishes the contour of the ampoule throat 1 from the surroundings while the area bound within the shade line 5 contains information of the ampoule throat 1 to be detected, and accordingly, the area bound within the shade line 5 can be examined.

Figure 5A:
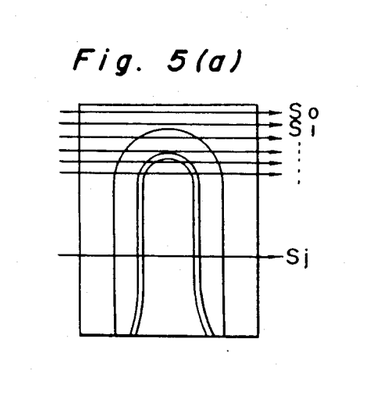
FIGS. 5(a) and 5(b) are diagrams used to explain the processing of data representative of the image shown in FIG. 4.
Figure 5B:
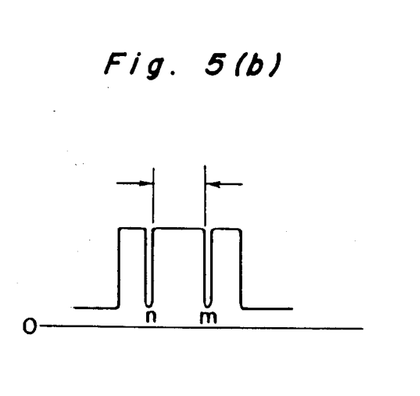

In view of the foregoing, if a video camera for visualizing the image so obtained scans the image sequentially with horizontal scan lines So, Sl, ... and Sj, as shown in FIG. 5(a), to provide an electric signal indicative of the image of the ampoule throat 1, a waveform as shown in FIG. 5(b) can be obtained for each of the horizontal scan lines So, Sl, ... and Sj. The waveform shown in FIG. 5(b) is shown having two voltage drops n and m representative of the opposite lateral portions of the wall of the ampoule throat 1, which drops result from the shade line 5 shown in FIG. 4. By detecting the voltage drops n and m in the electric signal obtained for each of the horizontal scan lines, the region of the ampoule throat 1 which is to be detected can be determined. Thus, even though the shape and/or outer diameter of the substantially transparent container desired to be examined varies, the detection region of such substantially transparent container can be automatically determined with no manual intervention required. This is the most important point of the present invention.

Since as hereinbefore discussed the detection region of the substantially transparent container which is desired to be examined can be automatically determined according to the present invention as the area bound inside the opposite lateral portions of the wall of such container, examination of the rays of light which have passed through such detection region of the substantially transparent container can result in a detection of the presence or absence of an abnormality in the substantially transparent container.

A preferred embodiment of an automatic inspecting system based on the foregoing principle according to the present invention will now be described with reference to FIGS. 6 to 8.

Figure 6:
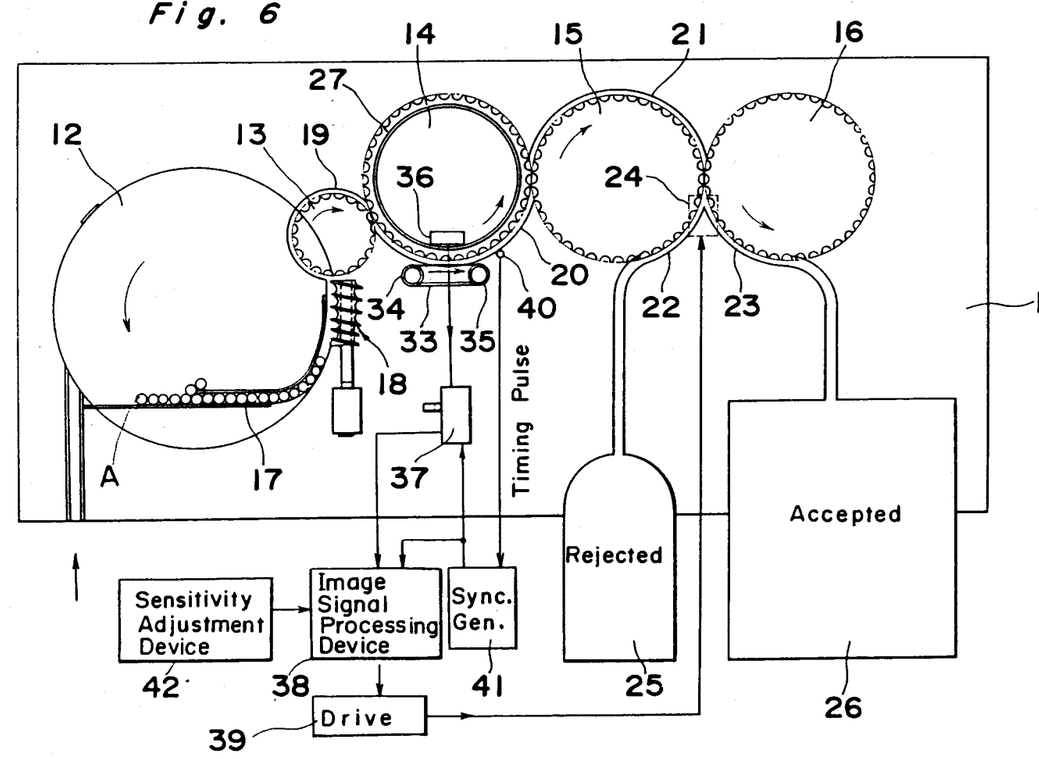
FIG. 6 is a schematic diagram showing the ampoule inspecting system according to the present invention.

As best shown in FIG. 6, a container inspecting machine comprises a generally rectangular table 11 having a turntable 12 for successively supplying ampoules A, a first star wheel 13 for transporting the ampoules A, a second star wheel 14, a third star wheel 15 and a fourth star wheel 16, rotatably mounted thereon in series with each other for rotating in respective directions shown by the arrows. The turntable 12 has a guide 17 fixed thereon and also a screw feeder 18 for feeding the ampoules A along the guide 17 towards a first transfer station. Each of the first to fourth star wheels 13 to 16 has its periphery formed with circumferentially equally spaced, generally semi-circular pockets for receiving the ampoules A one in each pocket. The pitch between each pair of neighboring pockets is equal in all of the first to fourth star wheels even though the number of pockets thereof may vary.

At the first transfer station, the ampoules A successively fed by the screw feeder 18 are transferred onto the first star wheel 13 with one ampoule A received in a respective pocket in the star wheel 13. As the ampoules A received in the respective pockets in the first star wheel 13 are transported from the first transfer station towards a second transfer station, where the first and second star wheels 13 and 14 meet, during the rotation of the first star wheel in the direction shown by the arrow, the ampoules A are backed up by a generally arcuate guard plate 19 and will not therefore detach from the first star wheel 13. At the second transfer station, the ampoules A transported by the first star wheel 13 are successively transferred onto the second star wheel 14 so that the ampoules received by the second star wheel 14 can be transported towards a third transfer station past an inspection station. As is the case with the transportation of the ampoules A by the first star wheel, the ampoules A are backed up by a generally arcuate guard plate 20 until they are transported to the third transfer station and will not therefore detach from the second star wheel 14.

Similarly, the ampoules A transported to the third transfer station where the second and third star wheels 14 and 15 meet can be successively transferred onto and transported by the third star wheel 15 towards a fourth transfer station while backed up by a generally arcuate guard 21. And, the ampoules A transferred onto the fourth star wheel 16 at the fourth transfer station can be transported along an arcuate guide 23 towards an "ACCEPTED" pool 26. It is to be noted that a switching deflector 24 is provided at the fourth transfer station for selectively directing some of the ampoules, which have been determined as being defective as a result of the inspection as will be described later, towards a guide 22 leading to a "REJECTED" pool 25 and the remaining ampoules, which have been determined as being acceptable as a result of the inspection, towards the guide 23 leading to the "ACCEPTED" pool 26.

Figure 7:
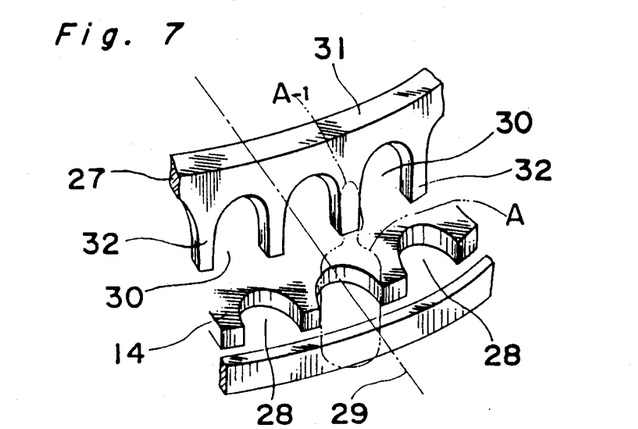
FIG. 7 is a fragmentary perspective view of a light absorbing ring used in the apparatus shown in FIG. 6.

As partially shown in FIG. 7, a light absorbing ring 27 forming the previously mentioned light absorbing member has defined therein openings 30 having a shape generally similar the inverted letter "U" and is coaxially mounted above the second star wheel 14 for rotating together with the second star wheel 14 with the openings 30 aligned with the respective pockets in the second star wheel 14. The light absorbing ring 27 is so supported and so positioned that each of the openings 30 can assume a position rearwardly of the corresponding ampoule A received in the associated pocket in the second star wheel 14 while allowing a portion of the light absorbing ring 27 around such opening 30 to be held generally rearwardly and to the side of and upwardly of an ampoule throat A-1 of such corresponding ampoule A. More specifically, the openings 30 are defined by making the light absorbing ring 27 in the form of a generally comb-shaped ring, that is, removing respective portions of the a ring to form the openings 30 while leaving circumferentially equally spaced teeth 32.

During the transportation of each of the ampoules A, carried by the second star wheel 14 past the inspection station, each ampoule is spun about its longitudinal axis in one direction. For this purpose, a generally endless rubber belt 33 trained between pulleys 34 and 35, one of said pulleys 34 being drivingly coupled with a drive motor (not shown), is disposed at the inspection station to cause each of the ampoules A to be spun when a bottom portion of each of the ampoules A is drivingly engaged with the endless rubber belt 34.

Also at the inspection station, a flat-panel type illuminator 36, which may be a strobe capable of effecting a uniform illumination, is disposed on one side of the light absorbing ring 27 opposite to the spinning belt 34 with respect to the path of movement of the ampoules A carried and transported by the second star wheel 14. On one side of the endless rubber belt 34 remote from the illuminator 36, there is disposed a video camera 37 which concurrently serves as a light sensor and a detecting means. This video camera 37 is electrically connected to an image signal processing device 38 so that an output signal from the video camera 37 can be supplied to the image signal processing device 38.

A sensor 40 is disposed at a predetermined location radially outwardly of the second star wheel 14 for generating a timing signal which is applied to a synchronizing signal generator 41 to produce a synchronizing signal so that the video camera 37 can be operated in synchronism therewith to record the image of each ampoule and also to check each ampoule to see whether it is acceptable or whether it is defective. More specifically, the determination of whether the ampoule inspected is acceptable or whether it is defective can be accomplished by inputting a preset level, defined by a sensitivity adjustment device 42, to a discriminator in the image signal processing device 38, causing the discriminator to determine if the waveform has a level drop of a magnitude exceeding the preset level, temporarily storing information indicative of the defective ampoule in a memory in the image signal processing device 38 if the waveform is found to have such a level drop, and providing, after the passage of a predetermined time, a rejection command which is applied to a drive unit 39 so that the switching deflector 24 can be brought in position to eject the defective ampoule from the third star wheel 15 into the guide into the "REJECTED" pool 25 as guided by guide 22. It is to be noted that a device for delaying, by a predetermined time, the results of discrimination made by the discriminator in the image signal processing device 38 can be embodied by a device that counts the number of the synchronizing pulses provided by the synchronizing signal generator 41.

Figure 8:
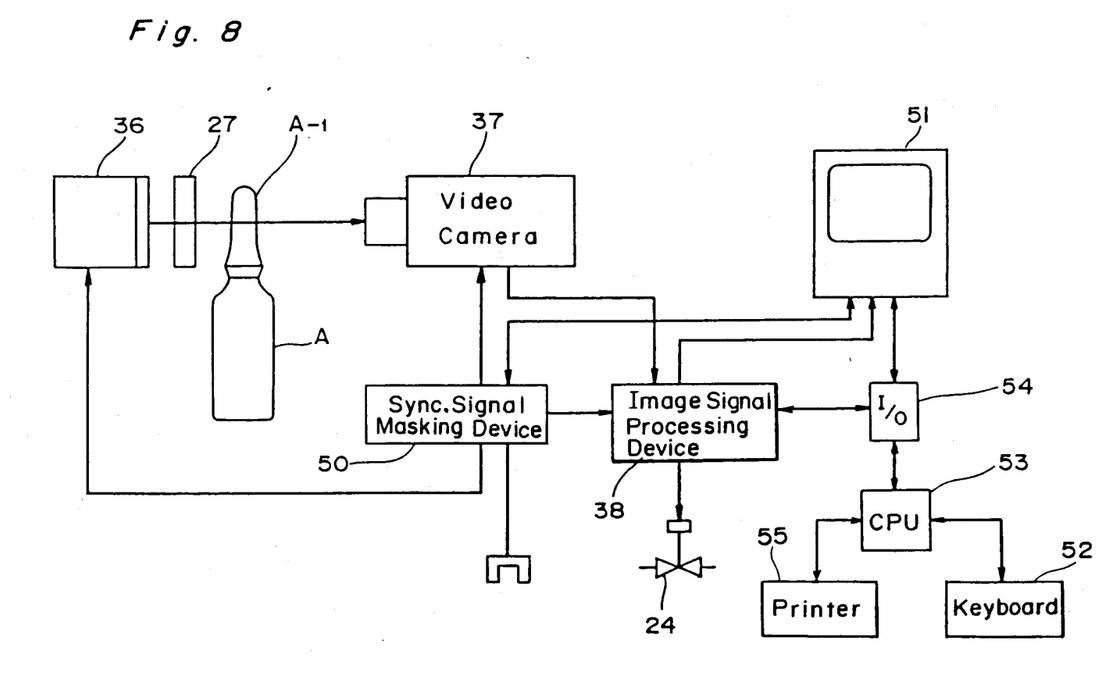
FIG. 8 is a block circuit diagram showing the details of an electric control system shown in FIG. 6.

The video camera 37 is, as best shown in FIG. 8, connected with the illuminator 36 through a synchronizing signal masking device 50 so that the illuminator 36 can be operated for a predetermined length of time for the purpose of accomplishing the inspection of the ampoules A at predetermined intervals by means of the video camera 37 synchronized therewith. The image obtained by the video camera 37 can be monitored by a display device 51 utilizing, for example, a cathode ray tube. All of the components of the system can be controlled by inputting commands through a keyboard 52 to a central processing unit (CPU) 53 which in turn controls them through an input/output interface 54. Results of the inspection performed can be recorded by a printer 55.

Figure 9:
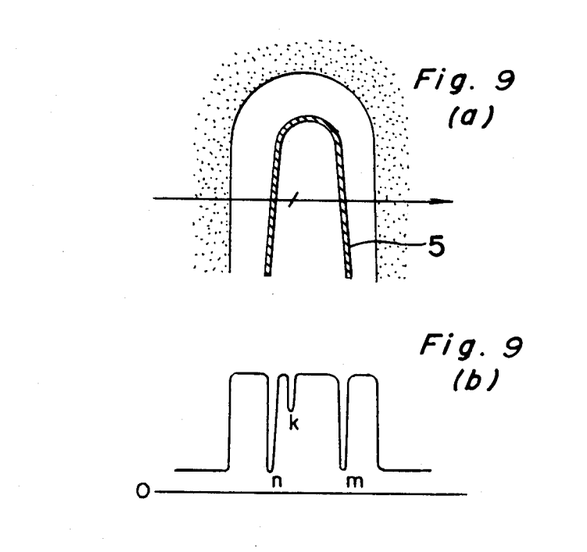
FIGS. 9(a) and 9(b) are explanatory diagrams used to explain the embodiment of the present invention.

FIG. 9(a) illustrates the image of the ampoule A which has been determined to be defective and FIG. 9(b) illustrates the waveform of one scan line which has traversed the ampoule throat of the defective ampoule A. A level drop k found in a portion of the waveform between the level drops n and m which defines the detection region corresponds to the presence of an abnormality in the ampoule throat and, therefore, it will readily be seen that, by processing such waveform as shown in FIG. 9(b), various deformities can be detected accordingly.

From the foregoing full description of the present invention, it has now become clear that, according to the present invention, the light absorbing member is disposed between the substantially transparent container and the illuminating light source to intercept the reflected rays of light and to restrict the range of the straight rays of light which have passed laterally outwardly of the substantially transparent container. Therefore, the mere placement of the light absorbing member is effective to accentuate the contour of the substantially transparent container against the bright background corresponding to the inside and outside the substantially transparent container. With the contour of the substantially transparent container so accentuated, the region of the substantially transparent container over which the inspection is to be made can be differentiated from the other regions. Therefore, any possible erroneous detection resulting from external noises can be substantially minimized, making the system of the present invention more reliable.

Also, since the region over which the inspection is to be made can be clarified irrespective of the shape of the substantially transparent container, the data processing can be easily accomplished.

Thus, the system of the present invention can be widely applicable in detecting the presence or absence of cracking in the wall forming the container, a bending of a throat of the container laterally from the longitudinal axis of such container, a filament-like bleeder left unremoved at the closed tip of the container throat, a variation in wall thickness of the container, and undesirable adherence of foreign matter to one or both of the inner and outer surfaces of the container.

Although the present invention has been described in connection with the preferred embodiment thereof with reference to the accompanying drawings, it is to be noted that various changes and modifications will become apparent to those skilled in the art. By way of example, although the light absorbing member has been shown and described as movable together with the second star wheel 14, a light absorbing member having only one opening 30 defined therein and fixed relative to the second star wheel 14 may be employed.

Also, each of the ampoules carried by the second star wheel 14 has been shown and described as spun about its longitudinal axis so that the entire region of the ampoule about the longitudinal axis thereof can be inspected. However, if desired, a switching means may be provided for switching the orientation of the substantially transparent container so that a plurality of regions of the container can be inspected.

Moreover, the illuminator and the light absorbing member may be reversed in position relative to each other and, in this case, the contour of the substantially transparent container can be accentuated by a bright line against a dark background. This technique may be useful for inspecting the shape of the container or detecting the presence or absence of surface projections or foreign matter sticking to the surface of the container.

Accordingly, such changes and modifications are to be understood as included within the scope of the present invention as defined by the appended claims.

What is claimed is:

1. A container inspecting apparatus for inspecting substantially transparent containers, said apparatus comprising:

means for positioning a substantially transparent container of a predetermined size at an inspection position in the apparatus;

illuminating light means, disposed to one side of the substantially transparent container of a predetermined size to be inspected when positioned at said inspection position, for illuminating the substantially transparent container positioned at said inspection position with rays of light including first rays of light consisting of tangential rays propagating tangentially to the outer periphery of the substantially transparent container of a predetermined size and straight rays propagating outwardly of the tangential rays with respect to the container, and second rays of light which propagate through the substantially transparent container of a predetermined size;

light receiving means, disposed to the other side of the substantially transparent container to be inspected when positioned at said inspection position, for receiving the rays of light from said illuminating light means;

a light shielding member having an edge defining an opening therethrough, said edge extending outwardly a predetermined distance from the tangential rays of light of said illuminating light means so that said opening defines areas each having a predetermined width as taken between said tangential rays and said edge in the plane of said opening through which opening said tangential and said straight rays can propagate to said light receiving means, and said light shielding member having said edge being so disposed relative to the substantially transparent container of a predetermined size, when positioned at said inspection position, such that said light shielding member shields said light receiving means from rays of light which would be reflected at surfaces of the substantially transparent container of a predetermined size, when positioned at said inspection station, and would travel to said light receiving means; and detecting means operatively associated with said light receiving means for analyzing said second rays to detect an abnormality in the substantially transparent container.

2. The apparatus as claimed in claim 1, further comprising a spinning means for spinning the container, when positioned at said inspection position, about a longitudinal axis thereof.

3. The apparatus as claimed in claim 1, further comprising a switching means for switching the orientation of the container, when positioned at said inspection position, so that a plurality of regions of the container can be inspected selectively.

4. The apparatus as claimed in claim 1, further comprising means operatively connected to said illuminating light means for operating the illuminating light means only for a predetermined time thereby enabling the container to be inspected at predetermined intervals.

5. The apparatus as claimed in claim 1, wherein one side of the light shielding member confronts the container, when positioned at said inspection position, and is light absorbent with respect to said rays of light which would be reflected in the apparatus.

6. The apparatus as claimed in claim 1, wherein said detecting means comprising a camera means for scanning a light image of the container formed by the light of the illuminating light means, and for providing an electric signal representative of said image.

7. The apparatus as claimed in claim 1, wherein said light receiving means and said detecting means comprise a video camera including an integrated light receiving and processing device.

8. The apparatus as claimed in claim 1, further comprising means for moving both the container and the light shielding member past an inspection station at which said inspection station is defined, said illuminating light means and said light receiving means being disposed on respective sides of the light shielding member and the container when positioned at the inspection station.

9. The apparatus as claimed in claim 1, further comprising means for successively moving a plurality of substantially transparent containers past an inspection station at which said inspection position is defined, all of said illuminating light means, said light shielding member and said light receiving means being disposed at the inspection station.

* * * * *